United States Patent [19]
Ali et al.

[11] Patent Number: 5,554,367
[45] Date of Patent: Sep. 10, 1996

[54] COMPOSITIONS FOR TREATMENT OF GLAUCOMA

[75] Inventors: Yusuf Ali; Rajni Jani; George R. McCarty, all of Forth Worth, Tex.

[73] Assignee: Alcon Laboratories, Inc., Fort Worth, Tex.

[21] Appl. No.: 334,512

[22] Filed: Nov. 4, 1994

Related U.S. Application Data

[63] Continuation-in-part of Ser. No. 188,284, Jan. 28, 1994, abandoned, which is a continuation-in-part of Ser. No. 89,358, Jul. 9, 1993, abandoned, which is a continuation of Ser. No. 480,406, Feb. 15, 1990, abandoned, which is a continuation of Ser. No. 154,514, Feb. 5, 1988, Pat. No. 4,911,920, which is a continuation of Ser. No. 890,519, Jul. 30, 1986, abandoned, which is a continuation of Ser. No. 667,003, Oct. 31, 1984, abandoned.

[51] Int. Cl.$^6$ .................................................. A61K 31/78
[52] U.S. Cl. .................. 424/78.04; 424/78.31; 424/78.37; 514/385; 514/913
[58] Field of Search .................................. 514/913, 385; 424/19, 78.04, 79, 81

[56] References Cited

U.S. PATENT DOCUMENTS

| | | | |
|---|---|---|---|
| 4,252,984 | 2/1981 | Manoury et al. | 564/349 |
| 4,311,708 | 1/1982 | Manoury et al. | 424/330 |
| 4,342,783 | 8/1982 | Morselli et al. | 424/330 |
| 4,474,751 | 10/1984 | Haslam et al. | 424/78 |
| 4,911,920 | 2/1988 | Jani et al. | 424/78 |

FOREIGN PATENT DOCUMENTS

| | | |
|---|---|---|
| 0525475A3 | 4/1987 | European Pat. Off. . |
| 0590786A1 | 1/1988 | European Pat. Off. . |
| 253717 | 1/1988 | European Pat. Off. . |

OTHER PUBLICATIONS

Jani, et al., "Ion Exchange Resins for Ophthalmic Delivery," *J. Ocul. Pharmacol.*, 10:1, pp. 57–67 (1994).

Varga, "Dei ersten Erfahrungen mit der Vistagan–und Betoptic Behandlung Glaukomkranker," *Folia Ophthalmol.*, 15:4, pp. 163–166 (1990);.

Maas, et al., "Efficacy and Safety of the Combination Therapy Pilogel/Beta–blocker: Interim Results," *Doc. Ophthalmol.*, 72:3–4, pp. 391–398 (1989); and.

Davies, et al., "Evaluation of Mucoadhesive Polymers in Ocular Drug Delivery.I. Viscous Solutions," *Pharm. Res.*, 8:8, pp. 1039–1043 (1991).

Becker et al., "Effective Reduction of Acute Toxicity of Certain Pharmacologic Agents," *Federation Proc.*, 17:348 (1958).

Becker et al., "Effective Reduction of the Acute Toxicity of Certain Pharmacologic Agents by Use of Synthetic Ion Exchange Resins," *Toxicol. Appl. Pharmacol.*, 1:42–54 (1959).

Stalker,"Enhancement of Ocular Drug Bioavailability Through the Use of Micronized, Functionalized Polymers as Carriers of Therapeutic Agents," A dissertation submitted in partial fulfillment of the requirements for the degree of Doctor of philosophy at the University of Kentucky, 1983.

*Primary Examiner*—Zohreh Fay
*Attorney, Agent, or Firm*—Sally Yeager

[57] ABSTRACT

Compositions for controlling glaucoma and ocular hypertension are disclosed.

10 Claims, No Drawings

COMPOSITIONS FOR TREATMENT OF GLAUCOMA

This is continuation-in-part of patent application Ser. No. 08/188,284, filed Jan. 28, 1994 now abandoned, which is a continuation-in-part of application Ser. No. 08/089,358, filed Jul. 9, 1993 now abandoned; which is a continuation of Ser. No. 07/480,406, filed Feb. 15, 1990 (abandoned); which is a continuation of Ser. No. 07/154,514, filed Feb. 5, 1988 now U.S. Pat. No. 4,911,920; which is a continuation of Ser. No. 06/890,519, filed Jul. 30, 1986 (abandoned); which is a continuation of Ser. No. 06/667,003, filed Oct. 31, 1984 (abandoned).

This invention is directed to compositions which are useful for the treatment of glaucoma and ocular hypertension.

BACKGROUND OF THE INVENTION

European Patent No. 253 717 discloses ophthalmic formulations containing combinations of specific beta adrenergic receptor antagonists (beta-blockers) and pilocarpine for the treatment of elevated intraocular pressure in patients refractory to treatment with beta-blockers alone. The patent discloses a beta-blocker concentration of 0.5 to 1.0 weight/volume percent (wt./v.%) and a pilocarpine concentration of 2 to 4 wt./v.%. The claimed formulation is made by combining lyophilized pilocarpine hydrochloride and a solution of an ophthalmic beta-blocker.

A product known as Normoglaucon has been sold in Germany. The product contains 2% pilocarpine and 0.1% metipranolol.

U.S. Pat. No. 4,474,751 discloses an ophthalmic drug delivery system using selected polymers which use the body temperature and pH to induce liquid to gel transition of the polymers. The patent discloses an extensive list of drugs which can be administered by the system, including a combination of timolol or R-timolol with pilocarpine. The specific examples do not describe any formulations of any drug combinations.

SUMMARY OF THE INVENTION

The present invention is directed to formulations for treating glaucoma and/or ocular hypertension in mammals, including humans. The formulations contain a combination of a beta-blocker, pilocarpine, a cation exchange resin, and a polyanionic polymer.

The invention is also directed to methods for treating glaucoma and/or ocular hypertension by topical administration of the formulations to the eye.

DESCRIPTION OF THE PREFERRED EMBODIMENTS

Many people suffering from glaucoma or ocular hypertension cannot control their elevated intraocular pressure (IOP) using beta-blockers alone. It is known that in many instances control can be gained by using an additional drug known to reduce intraocular pressure, such as pilocarpine, in combination with a beta-blocker. Pilocarpine is a cholinergic agonist that has been used for a long time to reduce intraocular pressure associated with glaucoma and ocular hypertension. While it is known to be relatively safe and effective, it does cause side effects, such as ocular discomfort, headache, and blurred vision. These side effects are uncomfortable for the patient and contribute to poor patient compliance. The present invention provides a formulation which is useful to those people requiring two drugs to control the elevated intraocular pressure associated with their glaucoma and/or ocular hypertension with a significant reduction in side effects.

The formulations of the present invention are believed to have the following advantages over known formulations: better patient compliance due to decreased side effects and by alleviating the need for two separate medications with different dosing regimens, better bioavailability of pilocarpine due to improved suspension properties, and reduced side effects.

The formulation of the present formulation contains about 0.1 to 1.0 weight/volume % (wt./vol. %) beta-blocker; about 0.25 to 10.0 wt./vol. % pilocarpine; about 0.05 to 10 wt./vol. % pharmaceutically acceptable ion exchange resin and about 0.01 to 5.0 wt./vol. % polyanionic polymer such as Carbomer 934P or 974P. Useful beta-blockers (e.g. betaxolol, timolol, befunolol, labetalol, propranolol, bupranolol, metaprolol, bunalol, esmalol, pindolol, carteolol, hepunolol, metipranolol, celiprolol, azotinolol, diacetolol, acebutolol, atenolol, isoxaprolol), polyanionic polymers, and ion exchange resins of the invention are disclosed in U.S. Pat. No. 4,911,920, from which this case descends, and which is incorporated herein by reference.

Since both pilocarpine and most beta-blockers are basic compounds, they readily bind with strongly acidic ion exchange resins, such as poly(styrene-divinyl benzene) sulfonic acid. Upon administration to the eye, the pilocarpine and beta-blocker relatively slowly disassociate from the resin. Although the beta-blocker, betaxolol, alone has been formulated with an ion exchange resin and a polyanionic polymer resulting in a more comfortable formulation (Betoptic® S, available from Alcon Laboratories, Inc.), it is unexpected that side effects associated with pilocarpine would be significantly reduced through use of the present formulation.

The stability of pilocarpine in solution is limited at physiological pH. Therefore, the formulations of the present invention are prepared in two parts. As shown in the examples, the pilocarpine portion (Part I) is prepared at or below about pH 5. The beta-blocker portion (Part II) is prepared at about pH 8. Mixing of the two parts by the patient, doctor, or pharmacist is required before application to the eye. The reconstituted formulation is close to physiological pH and is stable for about one month at room temperature.

The preferred reconstituted formulation contains 0.25% betaxolol base, 1.75% pilocarpine, 0.25% poly(styrene-divinyl benzene) sulfonic acid (Amberlite, Rohm & Haas), and 0.40% of Carbomer 934P (B.F. Goodrich). Betaxolol is a known compound, see U.S. Pat. Nos. 4,252,984, 4,311, 708, and 4,342,783.

The formulations of the present invention can be used to control glaucoma and ocular hypertension through topical administration to the eye one to four times daily according to the discretion of a skilled clinician.

The following examples are representative of formulations of the present invention and are not meant to be limiting.

EXAMPLE 1

| INGREDIENTS | PERCENT wt./vol. |
|---|---|
| PART 1 FORMULA | |
| Pilocarpine Hydrochloride | 8.75 |
| Sodium Hydroxide and/or Hydrochloric Acid | QS pH to 5.0 +/− 0.2 |
| Purified Water | QS to 100 |
| PART II FORMULA | |
| Betaxolol Hydrochloride | 0.35* |
| Poly(Styrene-Divinyl Benzene) Sulfonic Acid (Amberlite IRP-69 Hydrogen Form) | 0.313 |
| Carbomer 934P | 0.50 |
| Boric Acid | 0.10 |
| Mannitol | 2.20 |
| Disodium Edetate | 0.0125 |
| Benzalkonium Chloride, Solution | 0.0125 + 5% XS |
| Sodium Hydroxide and/or Hydrochloric Acid | QS pH to 8.0 +/− 0.2 |
| Purified Water | QS to 100 |

*Equivalent to 0.313% Betaxolol Base

Reconstitution of Parts I and II

The product composition after reconstitution (1 mL of Part I, and 4 mL of Part II, is given below. The entire contents of Part I are transferred to the Part II container and mixed well for 60 seconds.

Reconstituted Product

| INGREDIENTS | PERCENT wt./vol. |
|---|---|
| Betaxolol Hydrochloride, USP | 0.28* |
| Pilocarpine Hydrochloride, USP | 1.75 |
| Poly(Styrene-Divinyl Benzene) Sulfonic Acid (Amberlite IRP-69 Hydrogen Form) | 0.25 |
| Carbomer 934P, NF | 0.40 |
| Boric Acid, NF | 0.08 |
| Mannitol, USP, USP | 1.76 |
| Disodium Edetate, USP | 0.01 |
| Benzalkonium Chloride, Solution, NF | 0.01 + 5% XS |
| Purified Water, USP | 95–96 |

*Equivalent to 0.25% Betaxolol Base

EXAMPLE 2

| INGREDIENTS | PERCENT wt./vol. |
|---|---|
| PART 1 FORMULA | |
| Pilocarpine Hydrochloride | 8.75 |
| Sodium Hydroxide and/or Hydrochloric Acid | QS pH to 5.0 +/− 0.2 |
| Purified Water | QS to 100 |
| PART II FORMULA | |
| Betaxolol Hydrochloride | 0.35* |
| Poly(Styrene-Divinyl Benzene) Sulfonic Acid (Amberlite IRP-69 Hydrogen Form) | 0.313 |
| Carbomer 974P | 0.50 |
| Boric Acid | 0.10 |
| Mannitol | 2.20 |
| Disodium Edetate | 0.0125 |
| Benzalkonium Chloride, Solution | 0.0125 + 5% XS |
| Sodium Hydroxide and/or Hydrochloric Acid | QS pH to 8.0 +/− 0.2 |
| Hamposyl L | 0.0375 |
| Purified Water | QS to 100 |

*Equivalent to 0.313% Betaxolol Base

Reconstitution of Parts I and II

The product composition after reconstitution (1 mL of Part I, and 4 mL of Part II, is given below. The entire contents of Part I are transferred to the Part II container and mixed well for 60 seconds.

Reconstituted Product

| INGREDIENTS | PERCENT wt./vol. |
|---|---|
| Betaxolol Hydrochloride, USP | 0.28* |
| Pilocarpine Hydrochloride, USP | 1.75 |
| Poly(Styrene-Divinyl Benzene) Sulfonic Acid (Amberlite IRP-69 Hydrogen Form) | 0.25 |
| Carbomer 974P, NF | 0.40 |
| Boric Acid, NF | 0.08 |
| Mannitol, USP, USP | 1.76 |
| Disodium Edetate, USP | 0.01 |
| Benzalkonium Chloride, Solution, NF | 0.01 + 5% XS |
| Hamposyl L | 0.03 |
| Purified Water, USP | 95–96 |

*Equivalent to 0.25% Betaxolol Base

EXAMPLE 3

Formulations containing different beta-blockers at different concentrations and different concentrations of pilocarpine can be made by a person skilled in the art of making ophthalmic formulations.

| INGREDIENTS | PERCENT wt./vol. |
|---|---|
| PART 1 FORMULA | |
| Pilocarpine Hydrochloride | 1.25 to 50* |
| Sodium Hydroxide and/or Hydrochloric Acid | QS pH to 5.0 +/− 0.2 |
| Purified Water | QS to 100 |
| PART II FORMULA | |
| Beta-blocker | 0.125 to 1.252** |
| Poly(Styrene-Divinyl Benzene) Sulfonic Acid (Amberlite IRP-69 Hydrogen Form) | 0.125 to 1.252 |
| Carbomer 934P | 0.50 |
| Boric Acid | 0.10 |
| Mannitol | 2.20 |
| Disodium Edetate | 0.0125 |
| Benzalkonium Chloride, Solution | 0.0125 + 5% XS |
| Sodium Hydroxide and/or Hydrochloric Acid | QS pH to 8.0 +/− 0.2 |
| Purified Water | QS to 100 |

*Equivalent to provide for 0.25 to 10.0 wt./vol. % upon reconstitution.
**Equivalent to provide for 0.1 to 1.0 wt./vol. % upon reconstitution.

Reconstitution of Parts I and II

The product composition after reconstitution (1 mL of Part I, and 4 mL of Part II, is given below. The entire contents of Part I are transferred to the Part II container and mixed well for 60 seconds.

| Reconstituted Product | |
|---|---|
| INGREDIENTS | PERCENT wt./vol. |
| Beta-blocker | 0.1 to 1.0 |
| Pilocarpine Hydrochloride | 0.25 to 10.0 |
| Poly(Styrene-Divinyl Benzene) Sulfonic Acid (Amberlite IRP-69 Hydrogen Form) | 0.1 to 1.0 |
| Carbomer 934P, NF | 0.40 |
| Boric Acid, NF | 0.08 |
| Mannitol, USP, USP | 1.76 |
| Disodium Edetate, USP | 0.01 |
| Benzalkonium Chloride, Solution, NF | 0.01 + 5% XS |
| Purified Water, USP | 95–96 |

We claim:

1. A topical ophthalmic composition for controlling glaucoma and/or ocular hypertension comprising 0.1 to 1.0 wt./vol. % betaxolol, 0.25 to 10.0 wt./vol. % pilocarpine, 0.05 to 10.0 wt./vol. % poly(styrene-divinyl benzene) sulfonic acid, and 0.01 to 5.0 wt./vol. % polyanionic polymer selected from the group consisting of Carbomer 934P and Carbomer 974P.

2. The composition of claim 1 wherein the polyanionic polymer is Carbomer 934P.

3. The composition of claim 2 wherein the betaxolol concentration is 0.25%, the pilocarpine concentration is 1.75%, the resin concentration is 0.25%, and the Carbomer 934P concentration is 0.40%.

4. The composition of claim 1 wherein the polyanionic polymer is Carbomer 974P.

5. The composition of claim 4 wherein the betaxolol concentration is 0.25%, the pilocarpine concentration is 1.75%, the resin concentration is 0.25%, and the Carbomer 974P concentration is 0.40%.

6. A method for controlling intraocular pressure by topically applying to the eye a composition which comprises 0.1 to 1.0 wt./vol. % betatolol, 0.25 to 10.0 wt./vol. % pilocarpine, 0.05 to 10.0 wt./vol. % poly(styrene-divinyl benzene) sulfonic acid, and 0.01 to 5.0 wt./vol. % polyanionic polymer selected from the group consisting of Carbomer 934P and Carbomer 974P.

7. The method of claim 6 wherein the polyanionic polymer is Carbomer 934P.

8. The method of claim 7 wherein the betaxolol concentration is 0.25%, the pilocarpine concentration is 1.75%, the resin concentration is 0.25%, and the Carbomer 934P concentration is 0.40%.

9. The method of claim 6 wherein the polyanionic polymer is Carbomer 974P.

10. The method of claim 9 wherein the betaxolol concentration is 0.25%, the pilocarpine concentration is 1.75%, the resin concentration is 0.25%, and the Carbomer 974P concentration is 0.40%.

* * * * *